United States Patent [19]
Ali

[11] Patent Number: 5,905,034
[45] Date of Patent: May 18, 1999

[54] METHOD FOR PRECIPITATING NATURAL AVERMECTINS

[75] Inventor: Abdullah R. Ali, Mystic, Conn.

[73] Assignee: Pfizer Inc., New York, N.Y.

[21] Appl. No.: 08/891,198

[22] Filed: Jul. 10, 1997

Related U.S. Application Data

[62] Division of application No. 08/569,200, filed as application No. PCT/IB94/00080, Apr. 26, 1994, Pat. No. 5,686,274, which is a continuation of application No. 08/096,745, Jul. 23, 1993, abandoned.

[51] Int. Cl.$^6$ .............................. C12N 1/20; C12P 19/62; C12P 17/02
[52] U.S. Cl. ...................... 435/253.5; 435/76; 435/119; 435/123; 435/886
[58] Field of Search ................... 435/253.5, 119, 435/123, 886, 76

[56] References Cited

U.S. PATENT DOCUMENTS 5,206,155  4/1993  Omura et al. ........................ 435/71.3
5,234,831  8/1993  Hafner et al. ........................ 435/253.5

OTHER PUBLICATIONS

Schulman et al. Antimicrob. Agents Chemother. vol. 31(5), pp. 744–747, 1987.

*Primary Examiner*—Leon B. Lankford, Jr.
*Assistant Examiner*—Christopher R. Tate
*Attorney, Agent, or Firm*—Peter C. Richardson; Gregg C. Benson; A. Dean Olson

[57] ABSTRACT

A process for separating a natural B avermectin from a natural avermectin containing fermentation broth by using an aqueous precipitation. The process comprises extracting natural avermectins from the fermentation broth with a water miscible solvent and adding sufficient water to precipitate the natural B avermetins. Preferably, the water miscible solvent is a $C_1$–$C_3$ alcohol, acetone, or acetonitrile. In addition, an acid, base, salt or surfactant may be added to facilitate the precipitation. This invention provides an isolation technique that substitutes the use of an aqueous precipitation for nonaqueous solvent precipitations. The reduction in use of nonaqueous solvents provides economic, environmental and safety benefits.

1 Claim, No Drawings

METHOD FOR PRECIPITATING NATURAL AVERMECTINS

This is a division of application Ser. No. 08/569,200, filed on Jan. 16, 1996 now U.S. Pat. No. 5,686,274 under 35 U.S.C. §371 based on PCT/IB94/00080 filed on Apr. 26, 1994 which was a continuation of U.S. application Ser. No. 08/096,745 filed on Jul. 23, 1993 which is abandoned.

BACKGROUND OF THE INVENTION

The field of art to which this invention relates is processes for the isolation and purification of avermectin compounds, particularly processes for the extraction of avermectin compounds from a fermentation broth.

The avermectins are a group of broad spectrum macrolide anti-parasitic agents. They are produced by fermenting a strain of the microorganism *Streptomyces avermitilis* (e.g., ATCC 31267, 31271 or 31272 or mutants thereof) under aerobic conditions in an aqueous nutrient medium containing inorganic salts and assimilable sources of carbon and nitrogen. Typically, avermectins have been characterized by a nomenclature system that utilizes various letters and numbers to refer to specific substituents.

A subset of avermectins, the natural avermectins, includes compounds wherein the $C_5$ position is substituted by methoxy (denoted by A) or hydroxy (denoted by B); the $C_{25}$ position is substituted by secbutyl (denoted by a) or isopropyl (denoted by b); and the $C_{23}$ position is substituted by hydroxy (denoted by 2) or attached to the $C_{22}$ position by a double bond (denoted by 1). Thus, there are eight possible natural avermectins and specific compounds are referred to by using a combination of symbols such as B1a or B2b. In addition, a subset of the natural avermectins could be referred to, for example, by using the term B natural avermectins. The B natural avermectins refers to the four natural avermectins wherein the $C_5$ position is substituted by hydroxy, the $C_{25}$ position is substituted by either isopropyl or secbutyl and the $C_{23}$ position is substituted by hydroxy or is connected to the $C_{22}$ position by a double bond. The isolation and chemical structure of the eight natural avermectin compounds (sometimes referred to as the C-076 compounds) are described in detail in British Patent Specification No. 1573955.

There are a variety of processes for isolating avermectins from a growth medium and for the selective isolation of particular avermectins from a growth medium. For example, U.S. Pat. No. 4,423,211 describes a process wherein the pH of the fermentation broth is adjusted within the range of 1.5 to 6 with a mineral acid such as sulfuric, hydrochloric or nitric acid. Then, the broth is contacted with and agitated with an extractant such as toluene, and the avermectin components are dissolved into and taken up by the extractant. The solution comprising the avermectin and the extractant is then passed through a separator to strip off the extractant, and the remaining avermectin isolated by, for example, crystallization.

In addition, U.S. Pat. No. 5,077,398 describes a two step process in which B1 components are crystallized, from a concentrated water immiscible solvent extract of the avermectin containing broth, with an alcohol or hydrocarbon/alcohol mixture. B2 components are crystallized from the leftover extract (which remains after the B1 crystallization) subsequent to its supersaturation (e.g., by lowering the temperature) utilizing B2 seed crystals.

Although the above methods have advanced the art these methods still depend on the use of nonaqueous solvents and environmental concerns dictate the reduced use of solvents whenever possible. Thus, there is still a continuing search for new methods of isolating avermectins.

SUMMARY OF THE INVENTION

This invention is directed to a process for separating a natural B avermectin from a natural avermectin-containing fermentation broth by using an aqueous precipitation. The process comprises extracting natural avermectins from the fermentation broth with a water miscible solvent and adding sufficient water to precipitate the natural B avermectins. Preferably, the water miscible solvent is a $C_1$–$C_3$ alcohol, acetone, or acetonitrile. In addition, an acid, base, salt or surfactant may be added to facilitate the precipitation. Preferably, the acid, base or salt has a sodium, potassium, calcium, ammonium or hydrogen cation and a chloride, phosphate, sulfate, nitrate, bicarbonate, carbonate or hydroxide anion. The surfactant is preferably sodium lauryl sulfate.

This invention makes a significant contribution to the field of avermectin isolation by providing a method that substitutes the use of an aqueous precipitation for nonaqueous solvent precipitations. The reduction in use of nonaqueous solvents provides economic, environmental and safety benefits. The selectivity of the precipitation, which contributes to purification of the products, takes advantage of the strong dependence of the solubility of avermectins on water content in water miscible organic solvents. The process may be modified by the addition of various species (e.g., acid, base, salts, surfactant) to change the precipitate characteristics (e.g., granular, rather than oily precipitate) and to enhance selectivity of preferred components (e.g., B1 components over B2 components).

Other objects, features and advantages of the invention will be more apparent from the following detailed specification and claims.

DETAILED DESCRIPTION OF THE INVENTION

Any avermectin broth may be used in the process of this invention that contains the desired product, a natural B avermectin or mixture of such avermectins, preferably at a concentration of greater than about 0.2 grams/liter. By avermectin broth is meant an avermectin-containing medium that is the result of the fermentation of an appropriate culture, generally a strain of *Streptomyces avermitilis*. However, it is also meant to include the solids, or a suspension of the solids (containing most of the avermectins), that result from such fermentation. Such solids may be concentrated from the fermentation by methods such as centrifugation or filtration. The degree of effectiveness of the process depends on the concentration of the desired avermectin(s) in the broth due to the solubility characteristics of the avermectins and the solubility characteristics of impurities from the broth in aqueous solvent mixtures. Due to these characteristics, the yield of the desired avermectins and the quality of the product recovered by the process improve as the concentration of desired avermectin(s) in the broth increases. It is preferred that the broth concentration of the desired avermectin(s) is above about 0.2 grams/liter as this facilitates higher yields and improved product qualities.

Any water miscible solvent may be used to extract the natural avermectins from the above-described avermectin broth that is capable of extracting the natural avermectins and does not deleteriously affect the desired end product. Typically the water miscible solvent is a $C_1$–$C_3$ alcohol, acetone, or acetonitrile. Preferably, the solvent is a $C_1$–$C_3$ alcohol and it is especially preferred that the solvent be methanol. Any amount of solvent may be used that is capable of extracting the desired natural avermectins. Generally, about 150% to about 300% by weight of solvent relative to the broth or concentrated broth is used as below about 150% a significant amount of the desired natural avermectins remain associated with the solid phase of the broth slurry and above about 300% undesired fermentation by-products can be extracted and unnecessary solvent is used. Solids are removed from the extract by a standard method such as filtration or centrifugation.

Although water alone may be added to the avermectin water miscible solvent extract to selectively precipitate the desired natural B avermectins an acid, base, salt or surfactant (precipitation promoter) is typically added in conjunction with water to facilitate the precipitation. Preferably, the acid, base or salt has a sodium, potassium, calcium, ammonium or hydrogen cation and a chloride, phosphate, sulfate, nitrate, bicarbonate, carbonate or hydroxide anion. It is especially preferred that the acid, base, or salt is sodium chloride, potassium phosphate, sulfuric acid, sodium bicarbonate, sodium hydroxide or potassium hydroxide. The addition of sodium chloride or sodium bicarbonate is particularly advantageous because it improves the handling qualities of the precipitate. Although any surfactant may be used that facilitates the precipitation (e.g., provides for enhanced precipitate quality) it is preferred that the surfactant is anionic or cationic and especially preferred that the surfactant be an alkyl sulfonate such as sodium lauryl sulfate. In addition, combinations of the above described acids, bases, salts or surfactants may be used that facilitate the precipitation. For example, combinations of salts and surfactants such as sodium chloride and sodium lauryl sulfate are particularly advantageous because they provide precipitates with good purity and desirable handling characteristics.

Any amount of water may be used that is effective in selectively precipitating the natural B avermectins from the water miscible solvent broth extract. Generally, the amount of water added to precipitate the desired product depends on the initial water content of the extract and the concentration of the desired avermectin(s). The desired water concentration of the mixture after water addition varies from about 45% to about 75% by weight of the final mixture. Preferably, the water added produces a water concentration from about 50% to about 65% by weight of the final mixture. The preferred amount of water may vary depending on the type and amount of acid, base, salt, or surfactant addition. Thus, generally it is preferred to use more water if, for example, the above described additives are not used. In addition, the amount of water may be advantageously varied to achieve selective precipitation of the particular natural B avermectins. Thus, for example, the addition of less water will generally facilitate the selective precipitation of the B1 components over the B2 components.

Generally any amount of precipitation promoter may be used that is effective, in conjunction with water, in selectively precipitating the natural B avermectins from the water miscible solvent broth extract. Typically about 0% to about 8% by weight of the final mixture of salt is used and preferably, about 3% to about 5% by weight of the final mixture of salt is used. Typically about 0% to about 2% by weight of the final mixture of surfactant is used and preferably, about 0.1% to about 1% by weight of the final mixture of surfactant is used. Typically an amount of acid sufficient to provide a pH of about 2 to about 7 is used and preferably an amount of acid sufficient to provide a pH of about 2.5 to about 4 is used. Typically an amount of base sufficient to provide a pH of about 8 to about 11 is used and preferably an amount of base sufficient to provide a pH of about 8.5 to about 10 is used.

Generally the process of this invention is performed by extracting the natural avermectins from the fermentation broth with the water miscible solvent and adding sufficient water (and any desired precipitation promoter) to precipitate the natural B avermectins. Preferably, the fermentation broth biomass is concentrated, by for example centrifugation, filtration or ultrafiltration to about 4 to 12 times its initial concentration, and the appropriate amount of water miscible solvent is added to the resulting wet solids. The resultant slurry is mixed at sufficient intensity for a sufficient time to assure dissolution of the desired avermectins (generally about 1 to about 8 hours). The remaining suspended solids (containing biomass, fermentation byproducts, lipids, lipoproteins, etc.) are removed by centrifugation, filtration or ultrafiltration. Typically these process steps are performed at ambient temperatures although any temperature (e.g., about 15° C. to about 40° C.) may be used that does not significantly deleteriously affect the yield of the desired product.

The desired amount of water and any desired precipitation promoter are added to the resultant water miscible solvent fermentation broth extract. This addition is typically performed by batch addition while stirring. The solution is stirred for a sufficient time (e.g., 12 to 48 hours) to achieve the desired natural B avermectin precipitation. Again, this precipitation is conveniently carried out at ambient temperature although any temperatures (e.g., about 15° C. to about 40° C.) may be used that does not significantly deleteriously affect the yield of the desired product.

The resulting precipitates are collected by, for example, filtration and further purified. While the further purification can be accomplished by any means known to those skilled in the art (including, for example, chromatographic techniques or solvent-based recrystallizations such as those described in U.S. Pat. No. 5,077,398), it is preferred to use recrystallizations based on the use of water and the water miscible solvent used for the initial extraction. Thus, the precipitate is redissolved in the water miscible solvent and the desired product is recovered at higher purity by adding sufficient water and, optionally, salts and/or surfactant, to cause selective crystallization of the desired product. This procedure may be repeated until the desired purity of the product is obtained. The advantage of this method is that a single solvent is used for the entire recovery and purification process, which simplifies the reuse of the solvent with attendant economic and environmental benefits.

The process of this invention may be used to selectively precipitate the natural B avermectins collectively or it may be used to sequentially selectively precipitate a subset of the natural B avermectins such as the natural B1 avermectins (i.e., B1a, B1b) followed by precipitation of the remaining natural B2 avermectins.

It will be apparent to those skilled in the art that the process described above for the recovery of "natural" avermectins can be readily used for the recovery of other types of avermectins. Avermectins other than the "natural" ones described in British Patent Specification No. 1573955 include, for example, those described in U.S. Pat. No. 5,089,480. Thus, for example, avermectins having cyclohexyl or cyclopentyl substituents at the C-25 position may be recovered from fermentation broths containing them by application of this invention.

This invention provides a process for avermectins recovery which avoids the use of solvents such as toluene or chlorinated solvents, with their recognized safety hazards and environmental problems, and allows a single solvent recovery and purification process which facilitates solvent recycle or reuse. It also combines in one process step the concentration of avermectins from the fermentation broth with significant purification of the avermectins in general, and specifically of the more desirable components. Finally, it does not require preconcentration of the broth extract, resulting in potential savings in the cost of equipment to practice the process.

It should be understood that the invention is not limited to the particular embodiments described herein, but that various changes and modifications may be made without departing from the spirit and scope of this novel concept as defined by the following claims.

EXAMPLE 1

Fermentation

Avermectins were produced by fermentation of a mutant strain of *Streptomyces avermitilis*. The strain used, designated R69-73, was deposited under the terms of the Budapest Treaty in the American Type Culture Collection, Rockville, Md. 20852, U.S.A. under accession number ATCC 55453 on Jul. 20, 1993. This strain advantageously produces smaller amounts of the A (i.e., 5-O-methyl) type avermectins than the deposited strain from which it was derived (ATCC 31272). This property facilitates the production of the B type avermectins, which are known to be of greater efficacy than the A type avermectins.

Inoculum was prepared by growing the culture in Fernbach flasks (2.8 liters capacity) containing 500 ml of the following medium:

|  | grams/liter |
|---|---|
| Pharmamedia (cottonseed meal) | 15 |
| Ardamine pH (yeast extract) | 5 |
| Thinned starch | 20 |
| Calcium carbonate | 2 |

The medium was adjusted to pH 7.2 with sodium hydroxide and sterilized by autoclaving the flasks at 121° C. for 45 minutes before use. After seeding with the culture, the flasks were incubated for 72 hours at a temperature of 29° C. on a gyrotary shaker at a speed of 200 rpm. Two flasks were then used to inoculate the production fermenter, a 14 liter vessel containing 10 liters of the following medium:

|  | grams/liter |
|---|---|
| Glucose monohydrate | 45 |
| Peptonized milk nutrient | 24 |
| Ardamine pH (yeast extract) | 2.5 |
| P-2000 antifoam | 2.5 |

The medium was adjusted to pH 7.0 with sodium hydroxide and sterilized by autoclaving the flasks at 121° C. for 75 minutes. After cooling, the fermenter was supplied with air at a rate of 5 standard liters per minute and agitated at a speed of 600 rpm. Inoculation was performed with the flasks described above. Five days after inoculation, a continuous feed of glucose solution was started, providing 50 grams of glucose per day. The feed was continued until 13 days after inoculation, at which time the fermentation was harvested for recovery. The concentrations of avermectins at harvest, measured by HPLC, were as follows:

B1a-413, B1b-333, B2a-471, B2b-186 mg/liter.

Recovery

The fermentation broth (7 liters) was centrifuged to concentrate the biomass containing the avermectins. A total of 1163 grams (wet weight) of concentrated broth solids was obtained. To 581 grams of the wet solids was added 1200 ml of methanol. After thorough mixing to dissolve the avermectins, the aqueous methanol slurry was filtered to remove the suspended solids. The resulting methanol extract contained 39 weight percent water (by Karl Fischer titration) and contained the following concentrations of avermectins:

B1a-1146, B1a-822, B2a-1307, B2b-379 mg/liter.

The nonvolatile solids content of the filtered extract was 17.1 grams/liter. The ratio of B1a to total nonvolatile solids (purity of B1a) was 6.7%.

In each of the recoveries described in Table 1, 100 ml of the methanol extract solution described above was used. The additives listed in Table 1 were added and the solution was stirred for 24 hours at room temperature (23° C.). The resulting precipitates were collected by passing the suspension through a filter containing 3 grams of filteraid (i.e., calcined diatomaceous earth) supported on paper. The precipitate quality was characterized by observing the precipitate before and after filtration, and the results listed in Table 1. After washing the filter cake with 10 ml of aqueous methanol of approximately the same water content as the suspension that was filtered, the cake was suspended in methanol to redissolve the avermectin precipitates. The resulting solutions were assayed by HPLC to determine their avermectin contents. Samples of the solutions were dried to determine the total content of nonvolatile material. The B1a purities in Table 1 were calculated as the ratios of B1a content of the precipitate solutions to total nonvolatile solids content of the solutions.

TABLE 1

| Additives, Wt/vol. % | Final Water Content, wt. % | Precipitate Quality | B1a Yield to Precipitate | B1a Purity in Precipitate |
|---|---|---|---|---|
| Water only | 55% | oily | 79% | 25.5% |
| Water only | 60% | very oily | 81% | 22.5% |
| Water NaCl 4% | 55% | oily | 78% | 18.2% |
| Water NaCl 4% | 60% | oily | 86% | 19.5% |
| Water NaCl 4% NaLS* 0.2% | 55% | pasty | 71% | 19.7% |
| Water NaCl 4% NaLS* 0.2% | 60% | waxy | 82% | 20.8% |
| Water NaCl 4% NaLS* 0.2% | 65% | waxy | 61% | 14.6% |
| Water NaHCO$_3$ 2% | 55% | oily | 74% | 35.4% |
| Water K$_2$HPO$_4$ 2% | 55% | oily | 81% | 27.4% |
| Water H$_2$SO$_4$ to pH 3 | 55% | very oily | 73% | 21.5% |
| Water NH$_4$OH to pH 9 | 61% | oily | 82% | 27.3% |

*NaLS = Sodium lauryl sulfate

Additional purification was carried out by aqueous recrystallization of the avermectins from the methanol solutions by adding water, and repeating this process until the desired purity was obtained. For example, in this case 4% NaCl, 0.2% NaLS and 60% water were used for precipitation, after two recrystallizations, the product obtained was 95% avermectins by weight (approximately 75% B1a and 20% B1b).

EXAMPLE 2

Concentrated wet broth solids from Example 1, 582 grams, were mixed with 1200 ml of acetone to dissolve the avermectins. The aqueous acetone slurry was filtered to remove the suspended solids. The resulting acetone extract contained 41.9 weight percent water (by Karl Fischer titration) and contained the following concentrations of avermectins:

B1a-1393, B1b-999, B2a-1539, B2b-460 mg/liter.

The nonvolatile solids content of the extract was 16.9 grams/liter and the B1a purity of the extract (as defined above) B1a was 8.2%.

In each of the recoveries described in Table 2, 100 ml of the acetone extract solution described above was used. The additives listed in Table 2 were added and the solution was stirred for 24 hours at room temperature (23° C.). The resulting precipitates were collected by passing the suspension through a filter containing 3 grams of filteraid (i.e., calcined diatomaceous earth) supported on paper. After washing the filter cake with 10 ml of aqueous acetone of approximately the same water content as the suspension that was filtered, the cake was suspended in methanol to redissolve the avermectin precipitates. The resulting solutions were analyzed as described for those in Example 1, Table 1.

TABLE 2

| Additives, Wt/vol. % | Final Water Content, wt % | Precipitate Quality | B1a Yield to Precipitate | B1a Purity in Precipitate |
|---|---|---|---|---|
| Water only | 60% | oily | 75% | 20.3% |
| Water only | 70% | very oily | 91% | 22.1% |
| Water NaCl 4% | 60% | oily | 95% | 16.1% |
| Water NaCl 4% | 70% | oily | 97% | 16.4% |
| Water NaCl 4% NaLS* 0.2% | 60% | waxy | 75% | 16.9% |
| Water NaCl 4% NaLS* 0.2% | 70% | waxy | 87% | 15.4% |

As in Example 1, products with avermectin purities of 95% were obtained by repeating the crystallizations from methanol with water addition.

I claim:

1. A biologically pure culture of *Streptomyces avermitilis* ATCC 55453.

* * * * *